United States Patent [19]
Yun et al.

[11] Patent Number: 5,607,567
[45] Date of Patent: Mar. 4, 1997

[54] PROTAMINE-RESPONSIVE POLYMERIC MEMBRANE ELECTRODE

[75] Inventors: Jong H. Yun, Taegu, Rep. of Korea; Mark E. Meyerhoff; Victor C. Yang, both of Ann Arbor, Mich.

[73] Assignee: The Board of Regents Acting for and on behalf of University of Michigan, Ann Arbor, Mich.

[21] Appl. No.: 477,605

[22] Filed: Jun. 7, 1995

Related U.S. Application Data

[63] Continuation-in-part of Ser. No. 107,321, Aug. 16, 1993, Pat. No. 5,453,171, which is a continuation-in-part of Ser. No. 849,218, Mar. 10, 1992, Pat. No. 5,236,570.

[51] Int. Cl.$^6$ .................................................. G01N 27/26
[52] U.S. Cl. ........................ 204/418; 204/403; 204/415; 204/416; 435/287.1; 435/817; 435/24; 422/82.03; 205/777.5; 205/789.5; 205/792.5
[58] Field of Search ..................................... 204/418, 403, 204/416, 415; 435/817, 288, 291; 422/82.03; 205/789.5, 777.5, 792.5

[56] References Cited

U.S. PATENT DOCUMENTS

| | | | |
|---|---|---|---|
| 3,932,233 | 1/1976 | Ruzicka et al. | 204/418 |
| 4,770,759 | 9/1988 | Young et al. | 204/418 |
| 5,236,570 | 8/1993 | Ma et al. | 204/418 |
| 5,401,377 | 3/1995 | Shieh et al. | 204/418 |
| 5,417,835 | 5/1995 | Brown | 204/418 |

*Primary Examiner*—Bruce F. Bell
*Attorney, Agent, or Firm*—Rohm & Monsanto

[57] ABSTRACT

A polymeric membrane electrode gives potentiometric responses to macromolecules, such as protamine, in solution or biological specimens. A protamine-responsive membrane includes a lipophilic cation-exchange material for ionic macromolecules in a specially formulated plasticized, polymeric matrix material. Potentiometric response to protamine has been observed in membranes comprising 30–70 wt. % polymeric matrix material, such as polyvinyl chloride; 1–3 wt. % salt of a tetraphenylborate, such as potassium tetrakis(4-chlorophenyl) borate or salt of an organophosph(o-n)ate, such as calcium bis-[4-(1,1,3,3-tetramethylbutyl)phenyl] phosphate; and 30–70 wt. % of a plasticizer, such as 2-nitrophenyl octyl ether or tris (2-ethylhexyl) phosphate. The potentiometric response of these membranes to protamine can be used to study the binding interaction of protamine with heparin (both native and low molecular fractions) or to monitor protease activity, for example, by following the rate of degradation of intact protamine or a synthetic substrate by trypsin, as well as to measure protamine concentration in biological fluids, such as blood or plasma.

30 Claims, 6 Drawing Sheets

PROTAMINE-RESPONSIVE POLYMERIC MEMBRANE ELECTRODE

STATEMENT OF GOVERNMENT RIGHTS

This invention was made with government support under Grant Nos. R29-HL38353 and GM-28882 awarded by the National Institutes of Health. The government has certain rights in the invention.

RELATIONSHIP TO OTHER APPLICATION

This application is a continuation-in-part of U.S. Ser. No. 08/107,321 filed on Aug. 16, 1993, now U.S. Pat. No. 5,453,171 issued on Sep. 26, 1995 as a continuation-in-part of U.S. Ser. No. 07/849,218, filed Mar. 10, 1992, now U.S. Pat. No. 5,236,570 issued on Aug. 17, 1993. The disclosures of these applications are incorporated herein by reference.

BACKGROUND OF THE INVENTION

This invention relates generally to a polymer membrane type ion-selective electrode, and more particularly, to a polymer membrane type ion-selective electrode suitable for monitoring polycationic macromolecules such as protamine.

Polymer membrane type ion-selective electrodes are now routinely used in commercial biomedical instruments to measure accurately levels of clinical important small ions, such as $Ca^{++}$, $Na^+$, $K^+$, $Li^+$, $H^+$, and $Cl$, in undiluted serum, plasma, and whole blood. These ion-selective electrodes typically comprise a highly plasticized polymeric matrix material with an ion-exchange material or ion-complexing agent therein. The ion-exchange material may be a quaternary ammonium salt, such as tridodecyl methyl ammonium chloride (TDMAC).

Polyvinyl chloride (PVC) is a common polymeric membrane matrix material used in the art of solid-state or liquid-membrane electrodes for the detection of small ions (see, for example, U.S. Pat. No. 4,861,455 or Hartman, et al., "Chloride-Selective Liquid-Membrane Electrodes Based on Lipophilic Methyl-Tri-N-Alkyl-Ammonium Compounds and Their Applicability to Blood Serum Measurements," *Mikrochimica Acta* [Wein], 1978 II 235–246).

Efforts to develop similar sensors, including immuno-based biosensors, for the detection of large biomolecules, such as proteins or drugs, have thus far been unsuccessful. One of the most difficult problems has been identifying appropriate complexing agents and membrane chemistries that yield significant, specific and reversible electrochemical responses to the desired analyte. Even if a specific complexing agent is identified for a macromolecular biomolecule, whether the interaction with the macromolecular ion is strong enough to overcome the rather low mobility of a large ion to yield to significant electrochemical response remains in question. In theory, the sensitivity and selectivity of an ion-selective electrode membranes is governed by both the mobility of the analyte ion and the strength of the interaction between the ion-complexing agent and the analyte ion. In addition, strong interference resulting from a high concentration of small ions, such as chloride ions in a blood sample, may dictate the membrane's response.

U.S. Pat. No. 5,236,570, and its related patent application(s), disclose specially formulated polymer membranes which exhibit a large and reproducible potentionmetic response toward the polyanionic macromolecule heparin at clinically relevant concentrations. In preferred embodiments, heparin-selective membranes comprise poly(vinyl chloride) doped with a quaternary ammonium salt, such as tridodecyl methyl ammonium chloride, as an anion-complexing agent. The polyion response has been attributed to the development of a non-equilibrium steady-state-phase boundary potential change at the membrane/sample interface. The steady-state condition occurs when the flux of heparin extraction into the membrane from the sample solution via an ion-exchange reaction is equal to the flux of heparin into the bulk of the membrane. Because of the non-equilibrium response mechanism, the use of membranes with low plasticizer content (preferably less than 33%) yields sensors that respond to heparin at lower concentrations than conventional, more highly plasticized membranes (i.e., >66%). In other embodiments, successful membranes comprising silicone rubber do not require a plasticizer to achieve the appropriate flux conditions.

Heparin, of course, is an analyte of particular clinical significance since heparin is the anticoagulant drug used almost universally in surgical procedures and extracorporeal therapies, and for the prevention of thromboembolism following surgery or childbirth. Currently, protamine sulfate is the only available compound used to reverse heparin-induced anticoagulation. Protamine sulfate is a polycationic peptide (average $M_r$ is 4,500) derived from salmon sperm, sometimes designated salmine protamine or n-protamine. The major constituent of protamine is the basic amino acid arginine, a highly alkaline cationic substance. The basic guanadinium groups of protamine complex electrostatically with the sulfonate groups of heparin to render the anticoagulant activity of the heparin ineffective. Unfortunately, the use of protamine frequently results in adverse hemodynamic and hematologic side effects such as hypotension, bradycardia, pulmonary artery hypertension, depressed oxygen consumption, thrombocytopenia with pulmonary platelet sequestration, and leukopenia. There is, therefore, a need in the art for a method of clinically detecting the concentration of protamine in a biological fluid, such as blood or plasma.

Protamine is also used as a titrant in commercially available blood-clotting instrumentation to determine accurately heparin levels in blood. Because there are no aromatic amino acid residues (e.g., tyrosine) in protamine, conventional UV absorption methods can not be used to detect protamine in solution. Protamine interacts with conventional protein reagents, such as the Folin-phenol reagent and Coomassie brilliant blue G-250, and therefore, can be measured via either the Lowry or Bradford methods [see, for example, Lowry, et al., *J. Biol. Chem.*, Vol. 193, p. 265 (1951) or Bradford, et al., *Anal. Biochem.*, Vol. 72, p. 248 (1976)]. However, neither of these methods are specific for protamine. In addition, protamine is devoid of catalytic and enzymatic activities which could form the basis of an assay. Consequently, there is a need in the art for a means of quantifying protamine in solution, particularly in a complex medium, such as blood fluids, wherein a variety of proteins and other ionic species may be present.

Negatively charged lipophilic anions, such as tetraphenylborate derivatives, have been used in the art to make polymer membrane-type electrodes which are sensitive to organic cations including organic drug species, vitamins, and amino acids. These known sensors typically respond to hydrophobic organic cations based on their relative solubility in the organic membrane phase. There is, however, a need for a sensor which can detect a very hydrophilic species, such as protamine, which would not be expected to partition into the organic phase of a polymer membrane-type sensor.

It is, therefore, an object of this invention to provide an electrochemical sensor for ionic macromolecules.

It is another object of this invention to provide an electrochemical sensor for direct measurement of ionic macromolecules in whole blood or plasma.

It is also an object of this invention to provide an electrochemical sensor for direct measurement of ionic macromolecules in whole blood or plasma which is accurate over the expected clinically relevant concentration range.

It is a further object of this invention to provide an electrochemical sensor for direct measurement of ionic macromolecules in whole blood or plasma which possesses adequate dynamic response characteristics, i.e., responds rapidly to a change in ion concentration and returns promptly to baseline, so that it is suitable for continuous in vivo monitoring.

It is additionally an object of this invention to provide a polymeric membrane electrode having specific selectivity for biologically important macromolecules even in the presence of $Cl^-$ and other anionic impurities.

SUMMARY OF THE INVENTION

The foregoing and other objects are achieved by this invention which provides, in one embodiment, an ion-exchange membrane for cationic macromolecules, such as protamine, which is formed of a polymeric matrix material, a lipophilic cation-exchange material suitable for protamine detection, and a plasticizer. The cation-exchange material is dispersed or dissolved in the plasticized polymeric matrix material.

PVC has been found to produce potentiometric response to protamine when used as the polymeric matrix material of the ion-exchange membrane of the present invention. Although the examples herein are directed to formulations using PVC as the polymeric matrix material, it is to be specifically understood that other film-forming, hydrophobic polymers are suitable matrix materials. Various polymeric materials of the type used in electrode membranes can be used including synthetic and natural polymeric materials such as polymers and copolymers of ethylenically unsaturated monomers such as polyethylenes, poly(1,2-butadienes) and the like; polycondensation polymers, such as polyesters, polyamides, polyurethanes, etc., and silicone-based polymers, such as polydimethylsiloxane (e.g., silicone rubber). Such various polymers specifically include, without limitation, polyurethane, cellulose triacetate, poly(vinyl alcohol)/poly(vinylchloride) copolymer. For body-invasive, or in-line uses, of course, the polymeric matrix material should be biocompatible.

One or more plasticizers may be used, alone or in combination, in the membrane composition in order to maintain homogeneity of the mixture, as is known, and in order to control the flux of the polyion analyte to the surface of the membrane from the sample solution and the flux into the bulk of the polymer from the surface of the membrane, as will be described more completely hereinbelow. In accordance with the principles of the invention, when these two fluxes are equal, a steady-state non-equilibrium response is observed that is far greater than the equilibrium response predicted by a classical ion extraction mechanism governed by the Nernst equation.

A particularly preferred plasticizer, in these embodiments, is 2-nitrophenyl octyl ether. However, other plasticizers are suitable for preparing ion-exchange membranes in accordance with the present invention. Such other plasticizers include, without limitation, dioctyl phthalate, dioctyl sebacate, dioctyl adipate, dibutyl sebacate, dibutyl phthalate, 1-decanol, 5-phenyl-1-pentanol, tetraundecyl benzhydrol 3,3',4,4' tetracarboxylate, benzyl ether, dioctylphenyl phosphonate, tris(2-ethylhexyl) phosphate, and 2-nitrophenyl octyl ether, the other plasticizers listed on Tables II, IV, and V below. In selecting a plasticizer(s) for the polymeric membrane, it is important that the plasticizer be compatible with the polymeric matrix material. Incompatibility manifests itself, for example, by exudation of the plasticizer during curing, or by the formation of an opaque membrane. The result of incompatibility is membranes having shorter lifetimes and less reproducibility.

In embodiments using a silicone rubber as the polymeric matrix material, it may not be necessary to use an additional plasticizer, as set forth in U.S. Pat. No. 5,453,171.

The ion-exchange material is preferably a negatively charged lipophilic anion. Suitable ion-exchange materials include salts of organoborates, organophosphates, and organophosphonates. In particularly preferred embodiments of the invention, the salts of organoborates are tetraphenylborate derivatives. Illustrative tetraphenylborate derivatives, useful in the practice of the invention, include, but are not limited to, sodium tetraphenylborate, potassium tetrakis(4-chlorophenyl) borate, sodium tetrakis[3,5-bis(trifluoromethyl)phenyl]borate, potassium tetrakis[3,5-bis(trifluoromethyl)phenyl]borate, and the other tetraphenylborate salts list on Table I below. In a particularly preferred embodiments, the ion-exchange material is potassium tetrakis(4-chlorophenyl) borate.

In other preferred embodiments, particularly when the polymeric membrane is to be used in biological fluids, such as blood or plasma, the ion-exchange material preferably is a salt of an organophosphate or organophosphonate. The organophosph(on)ates are less sensitive to small ions, such as $K^+$ which are plentiful in blood, for example. Preferred salts of organophosphates or organophosphonates, include the salts set forth in Table IV herein, specifically including, but not limited to, tris (2-ethylhexyl) phosphate, dioctylphenyl phosphonate, and calcium bis-[4-(1,1,3,3-tetramethylbutyl)phenyl] phosphate. In a particularly preferred embodiment, the ion-exchange material is calcium bis-[4-(1,1,3,3-tetramethylbutyl)phenyl] phosphate.

Selectivity and sensitivity of the ion-exchange membranes are affected by the contents of the polymeric membranes. In preferred embodiments, potentiometric response to protamine has been observed with membranes comprising about 30–70 wt. % polymeric matrix material; about 30–70 wt. % plasticizer; and 0.1–5 wt. % cation-exchange material. The preferred cation-exchange material content is between about 1.0 and 1.5 wt %. The preferred polymer/plasticizer ratio is between the values of about 1.0 and 1.5.

In a particularly preferred embodiment for sensing protamine in solution, the ion-exchange membrane comprises about 1 wt % potassium tetrakis(4-chlorophenyl) borate, 49.5 wt % 2-nitrophenyl octyl ether, and 49.5 wt % poly(vinyl chloride). In another particularly preferred embodiment for sensing protamine in biological fluids, such as plasma, the ion-exchange membrane comprises 1.0 wt % bis-[4-(1,1,3,3-tetramethylbutyl)phenyl] phosphate calcium salt, 49.5 wt % tris (2-ethylhexyl) phosphate, and 49.5 wt % PVC.

In certain preferred embodiments, the ion-exchange membrane is prepared as a homogenous solution of the polymeric matrix material, plasticizer, and cation-exchange material in an organic solvent, such as tetrahydrofuran (THF) or dimethylformamide (DMF), which is suitable for casting into a thin film. The thin film can be cut to size for mounting on an electrode body as will be described hereinbelow. Typically, the membrane thickness is in the range of about 100 μm to 300 μm, preferably, ~200 μm. In other embodiments, the homogeneous solution can be coated and/or layered on a conductive metallic substrate or surface, such as a conductive wire.

In those embodiments wherein the polymeric matrix material is silicone rubber, the ion-exchange material preferably is combined with the silicone rubber after the silicone rubber has been dissolved in a suitable solvent. Subsequently, the silicone rubber mixture containing the ion-exchange material, is cast, or screen-printed, or otherwise installed, as a layer on a silicon-based integrated circuit chip, for example.

In accordance with an advantageous device embodiment of the invention, as ion-selective polymer membrane electrode which is responsive to protamine comprises:

(a) a housing containing a reference solution;

(b) an electrode arranged in the housing so that it is disposed in the reference solution; and (b) an ion-exchange membrane, in accordance with the present invention, disposed on one end of the housing so as to seal the reference solution inside the housing and to contact a sample solution external to the housing.

In further device embodiments, the protamine-responsive ion-exchange membranes of the present invention may be installed as a layer on a solid state sensor arrangement or and integrated circuit chip in accordance with the techniques described more completely in U.S. Pat. No. 5,453,171. In an integrated circuit chemical sensor arrangement of the invention, there is provided an input electrode of a conductive material in the vicinity of a region formed of a silicon-based semiconductor material, a permselective membrane having an electrochemical property responsive to protamine or other cationic macromolecule is arranged to be in adherence with the silicon-based semiconductor material and in electrical communication with the input electrode, for producing at the input electrode a voltage responsive to the electrochemical property.

In a method of use aspect of the present invention, the concentration of protamine in a liquid medium is measured as a function of its potentiometric response using a membrane electrode fabricated in accordance with the principles of the invention. The liquid medium may be a biological fluid, such as blood or blood components.

In a preferred method of use embodiment, however, the membrane electrode is pre-conditioned by soaking the membrane in a high concentration of analyte, illustratively, about 50 μg/ml of protamine sulfate for at least about 12–15 hours. The concentration of analyte used to pre-condition, or equilibrate, the membrane should be at least 50% of the expected concentration range of unknown analyte in solution. In clinical specimens, it is anticipated that the concentration of protamine will be in the range of 5 to 100 μg/ml.

After pre-conditioning, and prior to use, the membrane is exposed to a high concentration (e.g., 1–2M, and preferably 2M) of inorganic ions, such as NaCl or KCl, for a period of time sufficient to remove polyion analyte from the surface layers of the polymeric membrane, illustratively about 5 minutes. A 5 minute rinse with the same high-ionic strength solution regenerates the polymeric membrane electrode between uses. The time period, 5 minutes is illustrative, of course, and shorter or longer periods (e.g., 1–10 minutes, preferably 5 minutes or less) can be employed in the practice of the invention. It is preferred, however, that the selected time period be applied consistently, before and between measurements, so that the depth of surface depletion of analyte ions is kept consistent.

In another method of use embodiments, the ion-selective sensor of the present invention can be used to monitor proteolytic activity of proteolytic enzymes, such as trypsin, chymotrypsin, pepsin, and the like, by measuring the degradation of protamine, or the synthetic peptide substrate, as a function of its potentiometric response as the proteolytic enzyme(s) degrade the substrate into smaller fragments which do not produce a potentiometric response. In preferred embodiments, specially designed synthetic peptides comprising an amino acid sequence having at least an arginine trimer and an arginine dimer sequence connected by a hydrophobic amino acid residue is used.

BRIEF DESCRIPTION OF THE DRAWING

Comprehension of the invention is facilitated by reading the following detailed description, in conjunction with the annexed drawing, in which.

DETAILED DESCRIPTION

An understanding of the invention can be enhanced by reference to the following examples of specific embodiments.

In preferred embodiments of the present invention, a protamine-responsive polymer membrane is prepared which comprises:

| | |
|---|---|
| salt of a tetraphenylborate derivative | 2.0 mg |
| plasticizer | 66–132 mg |
| poly(vinyl chloride) | 66–132 mg |
| total | 200 mg |

A polymer casting solution is prepared by dissolving the dry ingredients in tetrahydrofuran (about 2 ml). This solution is cast into a glass ring (i.d.=22 mm) on a glass slide using a conventional method for ion-selective electrode (ISE) membrane preparation. The solvent is permitted to evaporate, illustratively overnight, to form a thin film of ~200 μm in thickness. Small disks (5 mm i.d.) are cut from the cast membrane and incorporated into Phillips electrode bodies (IS-561, Glasblaserei Moller, Zurich, Switzerland). A 0.12M NaCl solution is used as the internal filling solution.

Figure 1:
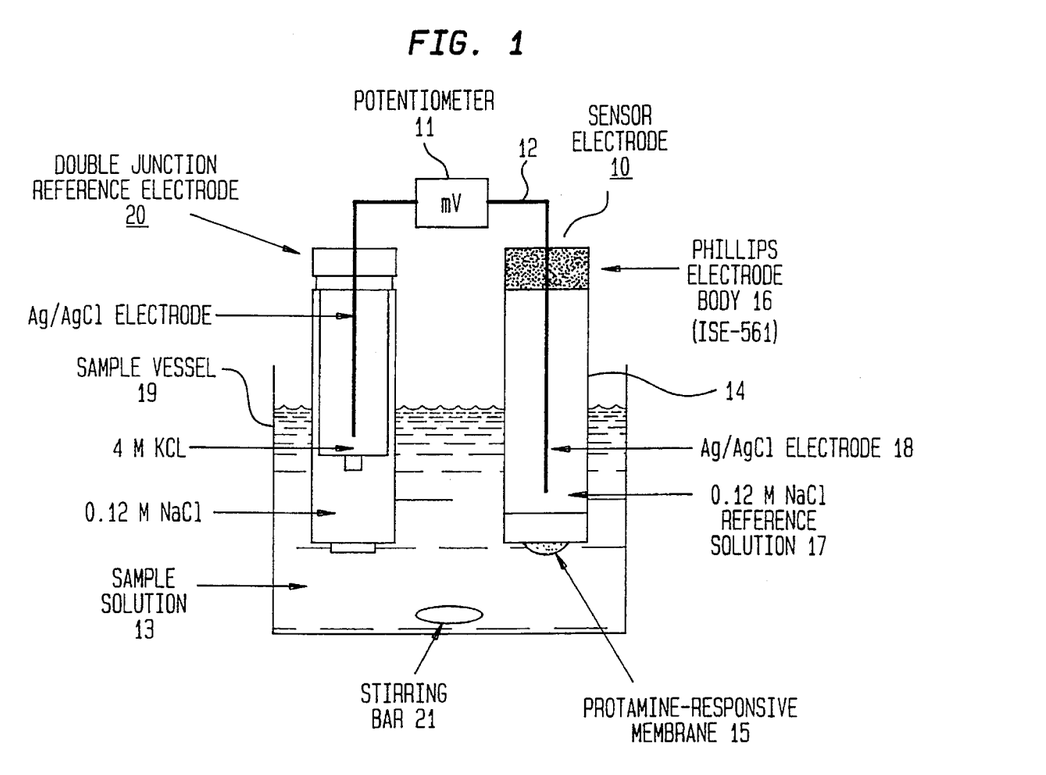
FIG. 1 is a schematic representation of an assembly for the measurement of an analyte solution with a protamine-responsive membrane electrode in accordance with the invention.

FIG. 1 is a schematic representation of an assembly for the measurement of an analyte solution with a protamine-responsive polymeric membrane electrode 10. In this embodiment of the invention, a thin protamine-responsive polymer membrane 15 constructed in accordance with the principles of the invention is mounted onto the tip of a conventional Phillips ISW-561 electrode body 16. Electrode body 16, includes housing 14 for containing a reference solution 17, in this case 0.012M NaCl, and a Ag/AgCl electrode 18 which is disposed in reference solution 17 and connected electrically by wire 12 to potentiometer 11 and reference electrode 20, in this case a Ag/AgCl double junction reference electrode. Protamine-responsive polymeric membrane 15 serves as the interface between sample solution 13 and reference solution 17.

Referring to FIG. 1, a potentiometric response of an analyte in sample solution 13 contained in sample vessel 19 is measured relative to outer Ag/AgCl double junction reference electrode 20 at ambient room temperature (~22° C.). Sample solution 13 is stirred with a magnetic stirring bar 21 during all experiments.

In accordance with the principles of the present invention, the electrode is conditioned by soaking the protamine-responsive membrane in 50 μg/ml protamine sulfate solution for 12–15 hours. Prior to measuring an unknown quantity of protamine in solution, the protamine-responsive membrane is exposed to a 2M KCl solution for 5 minutes. This high-ionic strength solution depletes the outer surface of the organic membrane of protamine (via ion exchange with potassium ions). Using colorimetric protein assays, it has been determined that 28 μg/cm$^2$ of protamine can be absorbed from a 50 μg/ml protamine solution after 12 hours of contact time, and 2.1 μg/cm$^2$ of absorbed protamine ion in the membrane is depleted by rinsing the membrane with 2M KCl solution for 5 minutes.

While salts of tetraphenylborate derivatives have been used as cation exchangers in polymer membranes for electrodes responsive to cationic drugs, a person of ordinary skill in the art would not expect such sensors to be analytically useful for the detection of polycations. One would expect the extraction of polyions with a high number of charges to yield, at equilibrium, a potentiometric response which is governed by the Nernst equation:

$$E_{elect} = K + (0.059/z)\log[\text{polyion}],$$

where $E_{elect}$ is the voltage of the ISE cell in volts, K is the cell constant for the ISE system, [polyion] is the concentration of polyion in the sample solution, and z is the charge on the polyion.

The charge of protamine, at or near neutral pH, can approach +20 or greater. Thus, a polymer membrane electrode responding to protamine via a classical ion extraction mechanism would be expected to yield a very small and impractical potentiometric response toward changes in protein concentration. In fact, this is the observed behavior for membranes doped with tetraphenylborate derivatives under equilibrium measurement conditions. Equilibrium potentials, measured after 24 hours of equilibration with protamine, are quite insensitive to protamine levels (i.e., have a response slope of ca. 4.5 mV/decade). However, we have discovered that if the outer layers of the pre-conditioned polymer membrane are devoid of polyion, then over a much shorter measurement period (e.g., 1–3 minutes), a very large (super-Nernstian) non-equilibrium steady-state potentiometric response to the polyion can be obtained at very low concentrations of the polyions. Therefore, in accordance with preferred method embodiments of the invention, the ion-responsive membrane is exposed to a high concentration of inorganic ions, illustratively NaCl or KCl, to remove polyion from the outer layers prior to making electrochemical measurements.

EXAMPLE 1

In a specific illustrative embodiment of the invention, a polymer membrane was formed having the following composition:

1 wt % potassium tetrakis(4-chlorophenyl) borate 33 wt % 2-nitrophenyl octyl ether; and 66 wt % poly(vinyl chloride)

Polymer membrane electrodes prepared with this composition yield a potentiometric response which is linear with the logarithm of protamine concentration over the range 0.1 to 1.0 μM in the presence of 0.12M NaCl. The fact that the membrane electrode responds potentiometrically to submicromolar levels of protamine in the presence of high levels of other cations (e.g., Na$^+$) indicates that the equilibrium constant for extraction of protamine into the membrane is quite favorable. In practical terms, this indicates that the electrode exhibits high selectivity for polycationic protamine over sodium ions.

Rapid response time and reversibility are important characteristics of a successful bioanalytical device. In order to evaluate whether the response of the protamine-responsive membrane electrode of the present invention is sufficiently rapid for practical analytical purposes, such as potentiometric titration, a potential versus time profile for the electrode was obtained following repetitive reversal of free protamine levels with stoichiometric amounts of heparin.

Figure 2:
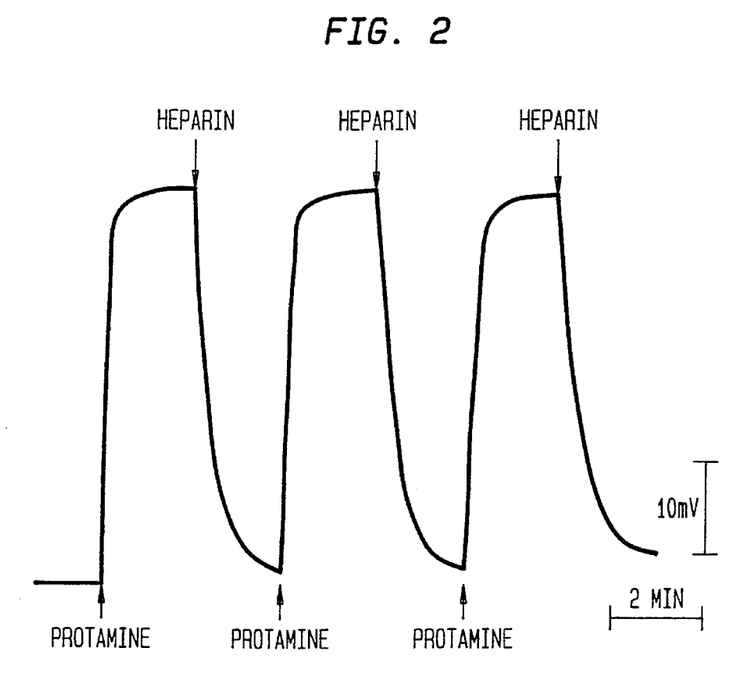
FIG. 2 is a potential versus time profile for a protamine-responsive membrane electrode following repetitive reversal of free protamine levels with stoichiometric amounts of heparin.

FIG. 2 shows a typical strip-chart recording of the potential changes after alternate sequential additions of a fixed amount of protamine sulfate (0.5 mg) and porcine mucosal heparin (65 units) to 50 ml of 0.12M NaCl background solution. Referring to FIG. 2, the response of the electrode toward the change of free protamine concentration in solution is relatively rapid (<2 minutes), reproducible, and almost completely reversible (i.e., the potential recovery measured at 3 minutes after heparin neutralization is between 92 and 97%). A substantially complete return to the baseline potential, following heparin neutralization, requires a longer equilibration time (5–12 minutes).

EXAMPLE 2

The magnitude and concentration range of the steady-state potentiometric response is controlled by the flux of the polyion into the surface of the membrane from the sample solution and into the bulk of the polymer membrane. When these two fluxes are equal, a steady-state non-equilibrium response is observed that is far greater than the equilibrium response predicted by the Nernst equation. For this reason, the magnitude and concentration range of polyion detectable is controlled by the plasticizer/polymer content of the polymer membrane, Of course, the cation-exchange material must be capable of extracting the polycation analyte into the organic phase of the membrane.

A series of PVC-based membranes doped with five different tetraphenylborate salts as the ion exchanger, plasticized with 2-nitrophenyl octyl ether in three different ratios of PVC/plasticizer (1:2, 1:1, and 2:1) were fabricated as described hereinabove. The compositions of the membranes are summarized on Table I below, with the weight percentages of the various components being given in parentheses. The potentiometric response of the polymer membranes toward polycationic protamine in 0.05M Tris-HCl buffer solution (pH 7.4) containing 0.12M NaCl was measured. The potential response is shown on the table as $\Delta E$ (mV) between an aqueous 0.12M NaCl solution and 10 μg/ml protamine sulfate in an aqueous solution of 0.12M NaCl.

The most significant potentiometric response, $\Delta E=41$ mV, occurred in the particularly preferred membrane composition:

1 wt % potassium tetrakis(4-chlorophenyl) borate;
49.5 wt % 2-nitrophenyl octyl ether; and
49.5 wt % PVC.

EXAMPLE 3

Various plasticizers, specifically the lipophilic alkyl/aryl alcohols, ethers/esters, and phosphates/diphosphonates, were employed as the membrane solvent and mediator for ion-selective electrode membranes in order to ascertain the effect of the type of plasticizer on the potentiometric response to protamine. The amount of ion exchanger, potassium tetrakis(4-chlorophenyl) borate, was kept constant at 1 wt %. The PVC/plasticizer ratio was varied from 1:2, 1:1, and 2:1. The compositions of the membranes are summarized on Table II below, with the weight percentages of the various components being given in parentheses. The potentiometric response of the polymer membranes toward polycationic protamine in 0.05M Tris-HCl buffer solution (pH 7.4) containing 0.12M NaCl was measured. The potential

TABLE I

| ion exchanger (wt %) | polymer (wt %) | plasticizer (wt %) | $\Delta E$, mV |
| --- | --- | --- | --- |
| sodium tetraphenyl-borate (1.0) | PVC (33.0) | 2-nitrophenyl octyl ether (66.0) | 3.0 |
| sodium tetraphenyl-borate (1.0) | PVC (49.5) | 2-nitrophenyl octyl ether (49.5) | 10.4 |
| sodium tetraphenyl-borate (1.0) | PVC (66.0) | 2-nitrophenyl octyl ether (33.0) | 9.6 |
| sodium tetrakis[3,5-bis(trifluoromethyl) phenyl-borate (1.0) | PVC (33.0) | 2-nitrophenyl octyl ether (66.0) | 15.2 |
| sodium tetrakis[3,5-bis(trifluoromethyl) phenyl-borate (1.0) | PVC49.5) | 2-nitrophenyl octyl ether (49.5) | 32.6 |
| sodium tetrakis[3,5-bis(trifluoromethyl) phenyl-borate (1.0) | PVC (66.0) | 2-nitrophenyl octyl ether (33.0) | 26.5 |
| sodium tetrakis[3,5-bis(trifluoromethyl) phenyl borate (1.0) | PVC (33.0) | 2-nitrophenyl octyl ether (66.0) | 13.3 |
| potassium tetrakis[3,5-bis(trifluoromethyl) phenyl borate (1.0) | PVC (49.5) | 2-nitrophenyl octyl ether (49.5) | 39.8 |
| potassium tetrakis[3,5-bis(trifluoromethyl) phenyl borate (1.0) | PVC (66.0) | 2-nitrophenyl oetyl ether (33.0) | 31.3 |
| potassium tetrakis (p-chlorophenyl) borate (1.0) | PVC (33.0) | 2-nitrophenyl octyl ether (66.0) | 12.2 |
| potassium tetrakis (p-chlorophenyl) borate (1.0) | PVC (49.5) | 2-nitrophenyl octyl ether (49.5) | 41.0 |
| potassium tetrakis (p-chlorophenyl) borate (1.0) | PVC (66.0) | 2-nitrophenyl octyl ether (33.0) | 33.4 |
| tetraphenylammonium tetraphenyl borate (1.0) | PVC (33.0) | 2-nitrophenyl octyl ether (66.0) | 2.0 |
| tetraphenylammonium tetraphenyl borate (1.0) | PVC (49.5) | 2-nitrophenyl octyl ether (49.5) | 3.7 |
| tetraphenylammonium tetraphenyl borate (1.0) | PVC (66.0) | 2-nitrophenyl octyl ether (33.0) | 3.9 |

According to Table I, most membranes exhibited significant response (i.e., $\Delta E>10$ mV) toward low levels of protamine. For each ion exchanger selected, particularly outstanding responses were observed in membranes having a 1:1 ratio of PVC/plasticizer, whereas the poorest responses were observed in membranes having a 1:2 ratio of PVC/plasticizer.

response is shown on the table as $\Delta E$ (mV) between an aqueous 0.12M NaCl solution and 10 μg/ml protamine sulfate in an aqueous solution of 0.12M NaCl.

TABLE II

| ion exchanger (wt %) | polymer (wt %) | plasticizer (wt %) | ΔE, mV |
|---|---|---|---|
| potassium tetrakis-(p-chlorophenyl) borate | PVC (33.0) | dioctyl sebacate (66.0) | 1.0 |
| | PVC (49.5) | dioctyl sebacate (49.5) | 2.8 |
| | PVC (66.0) | dioctyl sebacate (33.0) | 2.5 |
| | PVC (33.0) | dibutyl sebacate (66.0) | 0.5 |
| | PVC (49.5) | dibutyl sebacate (49.5) | 2.0 |
| | PVC (66.0) | dibutyl sebacate (33.0) | 2.5 |
| | PVC (33.0) | adipate (66.0) | 1.3 |
| | PVC (49.5) | adipate (49.5) | 3.8 |
| | PVC (66.0) | adipate (33.0) | 2.4 |
| | PVC (33.0) | thalate (66.0) | 8.2 |
| | PVC (49.5) | thalate (49.5) | 27.4 |
| | PVC (66.0) | thalate (33.0) | 24.6 |
| | PVC (33.0) | 2-nitrophenyl octyl ether (66.0) | 12.2 |
| | PVC (49.5) | 2-nitrophenyl octyl ether (49.5) | 41.0 |
| | PVC (66.0) | 2-nitrophenyl octyl ether (33.0) | 33.4 |
| | PVC (49.5) | tris (2-ethylhexyl) phosphate (49.5) | 24.5 |
| | PVC (49.5) | dioctylphenyl phosphonate (49.5) | 24.3 |
| | PVC (49.5) | 1-decanol (49.5) | 6.7 |
| | PVC (49.5) | benzyl ether (49.5) | 38.7 |
| | PVC (49.5) | 5-pheny-1-pentanol (49.5) | 0.9 |
| | PVC (49.5) | tetraundecyl benzhydrol 3,3',4,4' tetracarboxylate (49.5) | 3.6 |

As shown in Table II, the most significant electrochemical response toward clinical levels of protamine were exhibited by the membranes doped with 2-nitrophenyl octyl ether (membranes #5) and benzyl ether (membrane #9) and having PVC/plasticizer ratios of 1:1.

EXAMPLE 4

Protamine-responsive membranes were prepared using a preferred ion exchanger, potassium tetrakis(4-chlorophenyl) borate, at different concentrations. The PVC/plasticizer ratio was held constant at 1:1. Other membranes were prepared with a constant ion exchanger concentration (1 wt %) but varying ratios of PVC/plasticizer. The potentiometric response of the polymer membranes toward polycationic protamine in 0.05M Tris-HCl buffer solution (pH 7.4) containing 0.12M NaCl was measured and is shown on Table III as ΔE (mV) between an aqueous 0.12M NaCl solution and 10 μg/ml protamine sulfate in an aqueous solution of 0.12M NaCl.

TABLE III

| ion exchanger (wt %) potassium tetrakis-(p-chlorophenyl) borate | polymer (wt %) poly(vinyl chloride) | plasticizer (wt %) 2-nitrophenyl octyl ether | ΔE, mV |
|---|---|---|---|
| 0.5 | 49.5 | 49.5 | 35.3 |
| 1.0 | 49.5 | 49.5 | 41.0 |
| 1.5 | 49.5 | 49.5 | 42.4 |
| 2.0 | 49.5 | 49.5 | 40.6 |
| 3.0 | 49.5 | 49.5 | 38.3 |
| 5.0 | 49.5 | 49.5 | 27.5 |
| 1.0 | 33.0 | 66.0 | 12.2 |
| 1.0 | 39.0 | 60.0 | 24.3 |
| 1.0 | 60.0 | 39.0 | 43.4 |
| 1.0 | 66.0 | 33.0 | 33.4 |

The potentiometric response of the protamine-responsive membranes in Table III increases with increasing ion exchanger content to about 1.5 wt %. Then, the response decreases with increasing ion exchanger content. This is in contrast to conventional ion-selective electrodes for small ions wherein, above certain critical concentrations of ion exchanger, response to the selected small ion is essentially unchanged. As shown in this study, an optimal ion exchanger content is between about 1.0 and 1.5 wt % while an optimum PVC/plasticizer ratio is between the values of about 1.0 and 1.5.

Of course, these ratios may vary somewhat in membranes of other compositions made in accordance with the principles of the invention. For example, a series of PVC membranes were prepared with a 2:1 ratio of PVC/plasticizer (2-nitrophenyl octyl ether) and ion exchanger concentrations (potassium tetrakis(4-chlorophenyl) borate) ranging from 0.5 to 4.0 wt %. In these studies, the electrode response toward protamine increased with increasing concentration of ion exchanger to about 3 wt % and then leveled off. The reversibility of the electrode, however, decreased dramatically with an increase in the ion exchanger concentration. From a practical standpoint, a reduction in the magnitude of total potentiometric response may be an acceptable trade-off in order to obtain enhanced reversibility. This is especially true in embodiments where the sensor is to be re-used. For this reason, ion-selective membranes prepared with 1 wt % ion exchanger were used in the majority of the studies reported herein. However, it is to be understood that a person of ordinary skill in the art could adjust the sensitivity versus reversibility as required for any given purpose without departing from the principles of the invention.

EXAMPLE 5

In a preferred method of use embodiment, the protamine-responsive membrane electrode of the present invention is used to measure protamine levels in biological samples, such as whole blood or plasma samples. In clinical applications, the protamine sensor of the present invention can monitor protamine therapy in order to avoid overdose. Of course, other clinically important events, such as heparin rebound, can be monitored with the protamine sensor.

In these embodiments, it is anticipated that small cations, such as $K^+$ ions, which are present in plasma in a relatively high levels, could interfere with the operation of the sensor, particularly when salts of organoborates are used as the ion exchanger. Salts of organophosphates are less sensitive to K+ ions. Therefore, membranes for use in plasma or whole blood, preferably use salts of organophosphates as the ion-exchange material.

Membranes, comprising a 1:1 ratio of PVC/plasticizer, were doped with 1 wt % of a sample organophosphate or organophosphonate. The composition of the specimen membranes are set forth in Table IV. Table IV shows the potentiometric response of these membranes, as measured by potential change (ΔE) in mV, between an aqueous 0.12M NaCl solution and 10 μg/ml protamine in 0.05M Tris-HCl buffer solution (pH 7.4) containing 0.12M NaCl.

dibutyl sebacate, dioctyl adipate, and tris (2-ethylhexyl) phosphate resulted in the most significant response towards protamine. Unfortunately, the first three of these plasticizers were not compatible with the ion exchanger, $Ca(TBPP)_2$, resulting in opaque membranes with short lifetimes and less reproducibility.

Sample protamine-responsive membranes were tested in human plasma diluted 1:10 by vol. with 0.05M Tris-HCl buffer (pH 7.4) containing 0.12M NaCl and diluted human plasma further containing protamine in order to assess the potentiometric response of the membranes to clinically relevant samples. Referring to Table V, the potentiometric response of these membranes is shown to: (1) 10 μg/ml protamine in 0.05M Tris buffer containing 0.12M NaCl ($\Delta E_1$); (2) diluted human plasma ($\Delta E_2$); and (3) 50 μg/ml protamine in diluted human plasma ($\Delta E_3$).

TABLE IV

| ion exchanger (wt %) | plasticizer (49.5 wt %) | ΔE, mV |
| --- | --- | --- |
| tris (2-ethylhexyl) phosphate (1.0) | 2-nitrophenyl octyl ether | 10.8 |
|  | dioctyl sebacate | 2.7 |
|  | dibutyl sebacate | 3.4 |
|  | dioctyl adipate | 1.9 |
|  | benzyl ether | 12.2 |
| dioptylphenyl phosphonate (1.0) | 2-nitrophenyl octyl ether | 3.2 |
|  | dioctyl sebacate | 0.3 |
|  | dibutyl sebacate | −0.8 |
|  | dioctyl adipate | −1.5 |
|  | benzyl ether | 4.9 |
| bis-[4-(1,1,3,3,-tetramethylbutyl) phenyl]phosphate calcium salt (1.0) | 2-nitrophenyl octyl ether | 12.5 |
|  | dioctyl sebacate | 57.3 |
|  | dibutyl sebacate | 47.7 |
|  | dioctyl adipate | 41.0 |
|  | benzyl ether | 10.6 |
|  | tris (2-ethylhexyl) phosphate | 33.4 |
|  | dioctyl phenylphosphonate | 23.1 |
|  | 5-phenyl-1-pentanol | 0.2 |
|  | 1-decanol | 5.3 |

As shown in Table IV, the response toward protamine for membranes dopes with tris (2-ethylhexyl) phosphate and dioctylphenyl phosphonate was not nearly as significant as for those doped with the highly lipophilic bis-[4-(1,1,3,3-tetramethylbutyl)phenyl] phosphate calcium salt [Ca(TBPP)$_2$]. Among the plasticizers tested, dioctyl sebacate,

TABLE V

| ion exchanger (wt %) | PCV (wt %) | plasticizer (wt %) | $\Delta E_1$, mV[a] | $\Delta E_2$, mV[b] | $\Delta E_3$, mV[c] |
| --- | --- | --- | --- | --- | --- |
| potassium tetrakis-(p-chlorophenyl) borate (1.0) | 33.0 | 2-nitrophenyl-octyl ether (66.0) | 12.2 | 19.4 | 4.8 |
|  | 39.0 | 2-nitrophenyl-octyl ether (60.0) | 24.3 | 28.5 | 6.7 |
|  | 49.5 | 2-nitrophenyl-octyl ether (49.5) | 41.0 | 40.7 | 8.8 |
|  | 60.0 | 2-nitrophenyl-octyl ether (39.0) | 43.4 | 60.3 | 5.2 |
|  | 66.0 | 2-nitrophenyl-octyl ether (33.0) | 33.4 | 83.8 | 3.5 |
| bis-[4-(1,1,3,3-tetramethylbutyl)phenyl] phosphate calcium | 49.5 | dioctyl adipate (49.5) | 41.0 | — | 4.7 |
|  | 49.5 | dibutyl sebacate (49.5) | 47.3 | — | 8.5 |
|  | 49.5 | dioctyl sebacate (49.5) | 57.3 | — | 12.3 |
|  | 49.5 | tris (ethlhexyl)- phosphate (49.5) | 33.4 | 10.6 | 46.6 |
|  | 49.5 | dioctylphenyl-phosphate (49.5) | 23.0 | 25.4 | 4.2 |
|  | 49.0 | dioctyl sebacate (15.0) trioctyl phosphate (35.0) | 19.0 | 14.6 | 3.3 |
|  | 49.0 | dioctyl sebacate (25.0) trioctyl phosphate (25.0) | 33.7 | 21.5 | 17.2 |
|  | 49.0 | dioctyl sebacate (35.0) trioctyl phosphate (15.0) | 55.8 | 43.2 | 32.8 |
|  | 49.0 | dioctyl sebacate (40.0) trioctyl phosphate (10.0) | 57.2 | 29.6 | 25.7 |
|  | 49.0 | dioctyl sebacate (15.0) | 26.8 | 29.6 | 0.0 |

TABLE V-continued

| ion exchanger (wt %) | PCV (wt %) | plasticizer (wt %) | $\Delta E_1$, mV[a] | $\Delta E_2$, mV[b] | $\Delta E_3$, mV[c] |
|---|---|---|---|---|---|
| | | dioctyl phenyl-phosphate (35.0) | | | |
| | 49.0 | dioctyl sebacate (25.0) dioctyl phenyl-phosphate (25.0) | 32.4 | 27.0 | −2.1 |
| | 49.0 | dioctyl sebacate (35.0) dioctyl phenyl-phosphate (15.0) | 48.5 | 50.3 | 3.3 |

Most of the membranes tested yielded significant response towards plasma (see $\Delta E_2$). The outstanding exception was the membrane doped with Ca(TBPP)$_2$ incorporating tris (2-ethylhexyl) phosphate as a plasticizer. While this membrane yielded the lowest measured response to plasma ($\Delta E_2$=10.6 mV), it yielded the most significant response towards protamine in the presence of diluted plasma ($\Delta E_3$= 46.6 mV). Accordingly, the membrane doped with 1.0 wt % Ca(TBPP)$_2$ and having 49.5 wt % tris (2-ethylhexyl) phosphate and 49.5 wt % PVC appears to be most suitable for the measurement of protamine in clinically relevant samples.

A membrane doped with 1.0 wt % Ca(TBPP)$_2$ and having 49.5 wt % tris (2-ethylhexyl) phosphate and 49.5 wt % PVC was cast and mounted on an electrode body as described hereinabove. In a preferred method embodiment, the protamine-responsive polymer membrane electrode is pre-conditioned and washed to achieve better reversibility and reproducibility. In this specific illustrative embodiment, the membrane was pre-conditioned by soaking overnight (about 12–15 hours) in a 50 μg/ml protamine solution. The membrane was washed in 2M NaCl for 5 minutes before the first measurement to deplete the surface layers of the membrane of protamine ions and regenerated between measurements with the same washing procedure.

Figure 3:
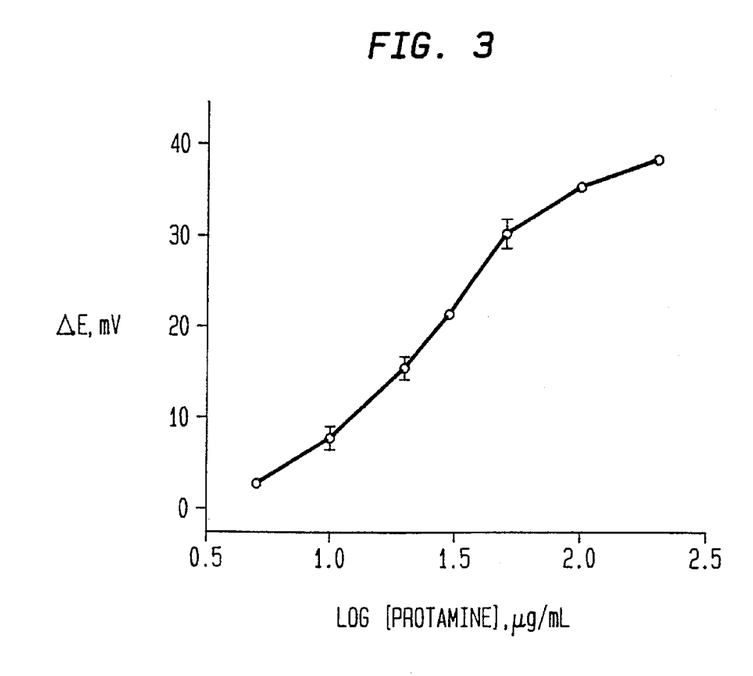
FIG. 3 is a graphic representation of the potentiometric response of a protamine-responsive polymer membrane electrode in accordance with the present invention plotted as the potential change, $\Delta E$ in mV, from the original cell potential against the logarithm of the concentration of a protamine analyte (μg/ml) in a clinical specimen of undiluted human plasma.

FIG. 3 is a graphic representation of the potentiometric response of the pre-conditioned protamine-responsive membrane as potential change, $\Delta E$ in mV, from the original cell potential plotted against the logarithm of the concentration of the protamine analyte (μg/ml) in undiluted human plasma. Referring to FIG. 3, a linear response region is observed at protamine levels between 5 and 100 μg/ml which coincides with the clinically relevant concentration.

EXAMPLE 6

In another method of use embodiment of the present invention, the protamine-responsive sensor is used to monitor trypsin activity. The use of electrochemical detectors to monitor biocatalytic reactions offers a number of advantages over conventional spectrophotometric methods, particularly in instances where catalytic activity must be detected in highly colored or turbid samples, such as cell suspensions. Since the protamine-responsive sensor of the present invention responds directly and reversibly to the presence of a native protein (i.e., protamine), it may be used to monitor the kinetics of certain proteases by following, potentiometrically, the rate of degradation of protamine as a substrate for a proteolytic enzyme, illustratively trypsin.

Trypsin is a primary representative of a large family of serine proteases. Many coagulation factors (e.g., factor Xa) and clot-dissolving enzymes, such as urokinase, possess trypsin-like activity. Trypsin catalyzes the hydrolysis of only those peptide bonds in a polypeptide chain in which the carbonyl function is donated by either lysine, or more preferably arginine. Current trypsin assays are all based on the use of synthetic chromogenic substrates (e.g., p-toluene-sulfonyl-L-arginine methyl ether). In addition to the high cost, the known synthetic substrates are small peptides, and not proteins. Therefore, catalytic activity toward these small synthetic peptide species may not accurately reflect the true proteolytic activity of trypsin. Nearly 50% of the amino acid content of protamine is arginine residues, as based on amino acid analysis. This characteristic makes protamine an ideal native protein substrate for trypsin.

Figure 4:
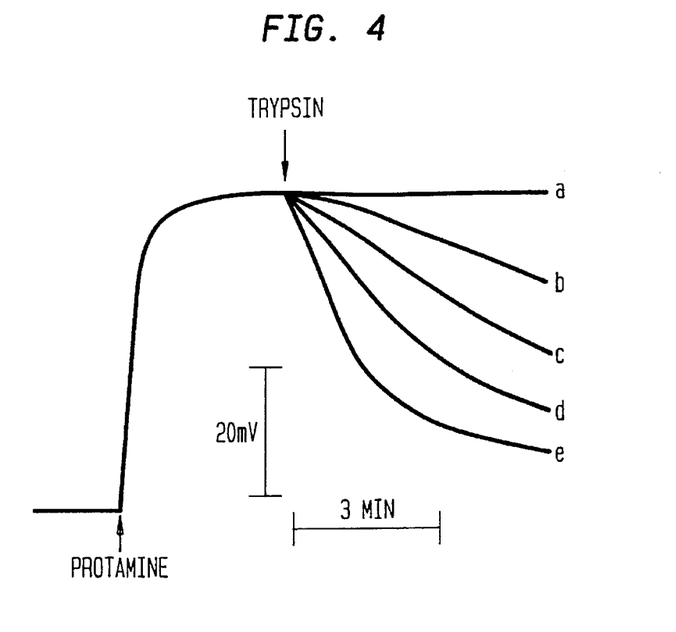
FIG. 4 is a plot of the time responses of a protamine-responsive polymer membrane sensor, used in accordance with the present invention, to monitor the digestion of protamine by trypsin of varying activity levels.

FIG. 4 is a plot of the time responses of a protamine-responsive polymer membrane sensor to digestion of protamine with varying levels of trypsin. The concentration of protamine sulfate in the sample solution was fixed at 20 μg/ml while the activity of the added trypsin was varied from 0–70 units/ml. All experiments were conducted at 22° C. in 0.05M Tris-HCl buffer (pH 7.6) containing 0.1M NaCl. The response curves are labelled (a) to (e) on FIG. 4 for the addition of trypsin having activities of 0 units/ml (a), 10 units/ml (b), 20 units/ml (c), 50 units/ml (d), and 70 units/ml (e), respectively. Referring to FIG. 4, the observed rate of potential decrease corresponds directly to the amount of trypsin added to a given concentration of protamine. Accordingly, FIG. 4 demonstrates that the protamine sensor of the present invention can be used to monitor the rate of protamine degradation by trypsin.

The rapid decrease in potentiometric response resulted from reduced extraction of the smaller protamine fragments, as produced by the trypsin reaction, into the polymer membrane phase of the electrode. The potentiometric response of the protamine sensor to more well-defined polycationic polypeptides of known chain length confirmed that the potentiometric response of the protamine-sensitive electrode of the present invention is highly dependent on the chain length of the polycationic analyte molecule. The magnitude of potentiometric response ($\Delta E$) toward a fixed concentration (10 μg/ml) of lysine monomer, trimer, and pentamer, low molecular weight poly-L-lysine ($M_r$ 3970) and high molecular weight poly-L-lysine ($M_r$ 58,100) in a 15 mM NaCl solution was 0, 3.5, 9.8, 22.3, and 33.2 mV, respectively.

Figure 5:
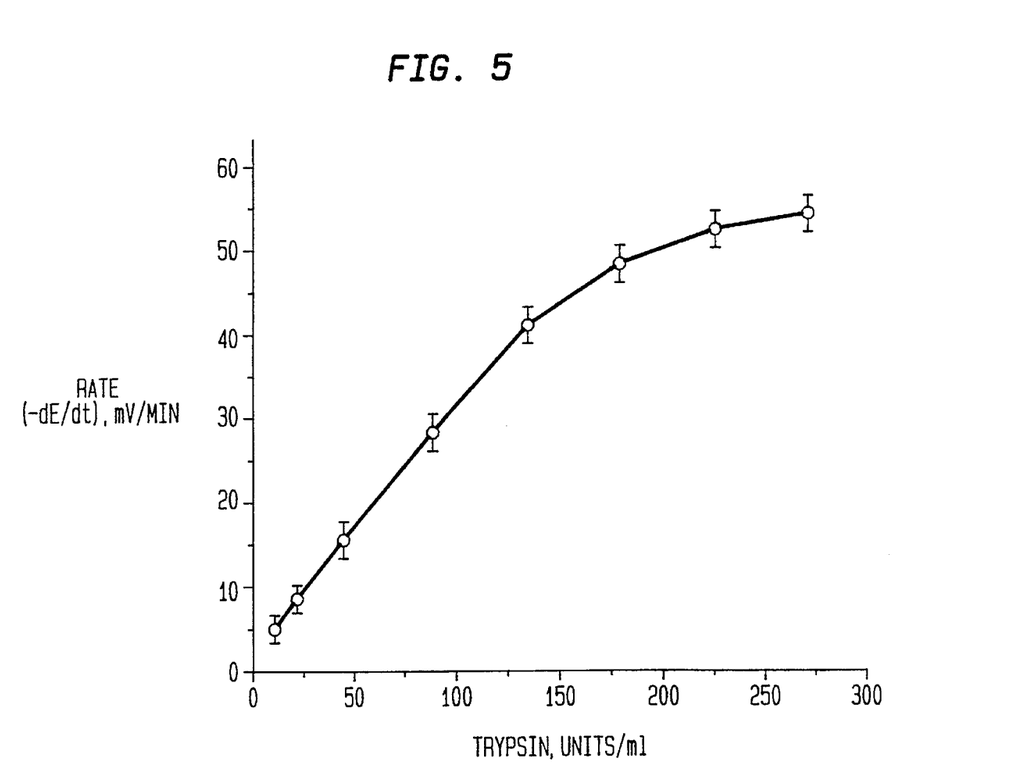
FIG. 5 is a calibration curve for determination of trypsin activity as measured by the rate of potential decrease ($-dE/dt$) in mV/min versus known trypsin activity in the range of 0–250 units/ml.

Trypsin activity, using protamine as the substrate, was measured by monitoring the time-dependent decrease in EMF of the protamine-responsive electrode. The initial rate of trypsin reaction, as measured by the rate of potential decrease (−dE/dt), using the protamine-responsive electrode, is linearly proportional to the activity of the added trypsin in the range of 0–130 units/ml as shown on FIG. 5 which is a calibration curve for determination of trypsin activity. The data shown on FIG. 5 are expressed as means±SD for four measurements made at room temperature (22° C.) in 0.05M Tris-HCl buffer (pH 7.6) containing 0.1M NaCl. The reaction rates were estimated by measuring the slopes of the initial potential decrease (–dE/dt) following the addition of different levels of trypsin to a fixed concentration of protamine (20 µg/ml).

The sensitivity of the electrochemical trypsin assay method of the present invention is highly dependent on the protamine concentration in the sample solution and can be increased by decreasing the concentration of protamine. The observed detection range for trypsin using the electrochemical assay is 10–200 units/mi. This is more sensitive than a known colorimetric titration method, for example, which is based on the measurement of p-nitrophenol released by the irreversible reaction of trypsin with a specific active site titrant, p-nitrophenyl-p'-guanidinobenzoate (500–25,000 units/ml). The sensitivity, speed, and simplicity of the electrochemical method make it an attractive alternative to classical spectrophotometric or titrimetric method for determining the proteolytic activity of trypsin. Furthermore, since the substrate protamine is a relatively large, naturally-occurring protein molecule, rather than a small synthetic peptide, the proposed assay may offer a more appropriate means to standardize trypsin activity assays.

EXAMPLE 7

In addition to monitoring trypsin activity as set forth in Example 6, the protamine-responsive sensor of the present invention can also be used to monitor the activity of other clinically important trypsin-like proteases, such as plasmin. A protamine sensor was constructed, in accordance with Example 5, having an ion selective membrane of the preferred composition:

1.0 wt % Ca(TBPP)$_2$ 49.5 wt % tris (2-ethylhexyl) phosphate; and 49.5 wt % PVC The potentiometric response to protamine ($\Delta E$=20 mV), as measured by this protamine sensor in the presence of 2 µg/ml protamine, was rapidly reduced by the addition of plasmin. Advantageously, the initial rate of digestion, as measured by the rate of potential decrease (–dE/dt), was proportional to the plasmin activity in the range of 0.01 to 0.5 units/ml. Alternately, since plasmin is the product of the enzymatic digestion of plasminogen by a plasminogen activator (namely a thrombolytic agent), the protamine sensor could also be used to monitor the activity of a thrombolytic agent, such as streptokinase, urokinase, or tissue plasminogen activator (t-PA).

EXAMPLE 8

Figure 6:
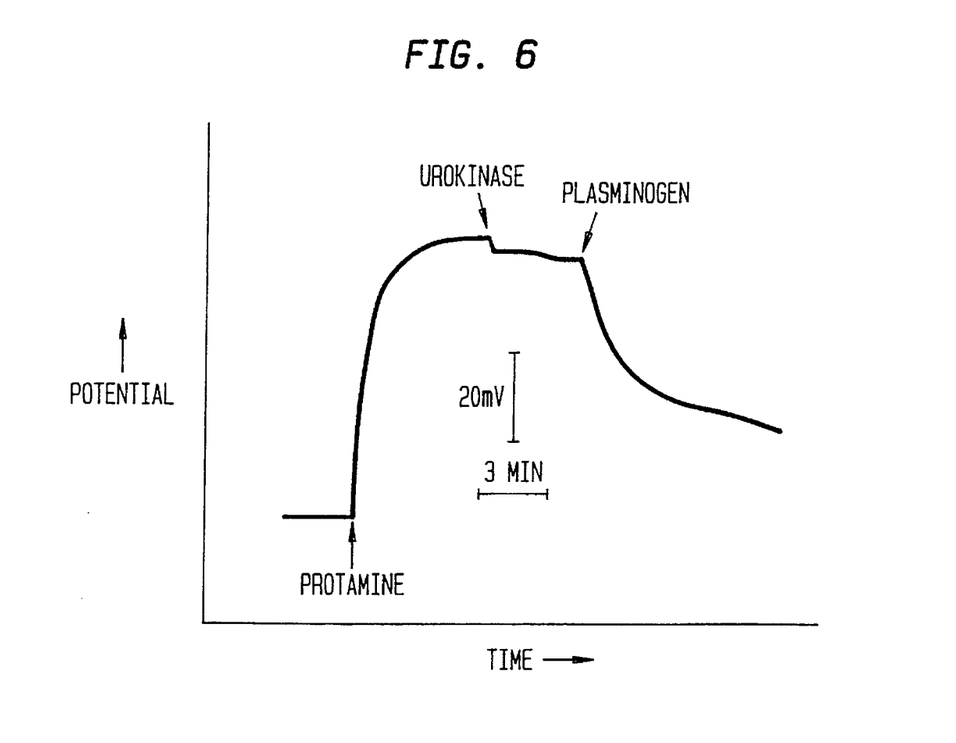
FIGS. 6 and 7 are graphic representations of the potentiometric response of protamine-responsive membrane electrodes over time as applied to direct potentiometric monitoring of urokinase activity in systems containing protamine, urokinase, and plasminogen.
Figure 7:
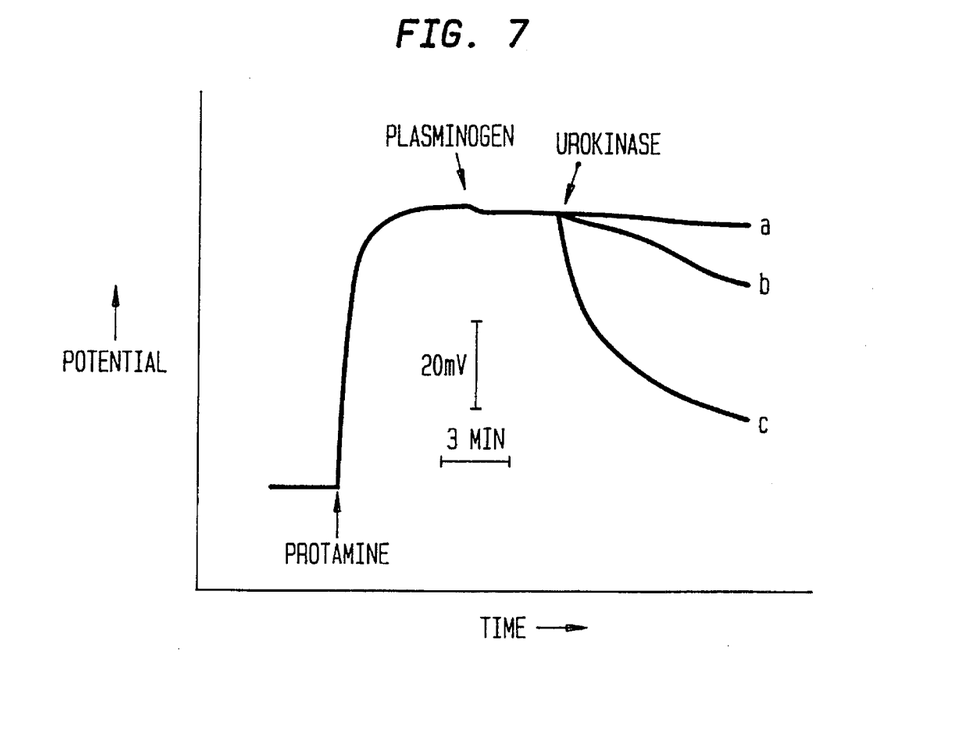

A membrane doped with 1.0 wt % Ca(TBPP)$_2$ and having 49.5 wt % tris (2-ethylhexyl) phosphate and 49.5 wt % PVC was cast and mounted on an electrode body as described hereinabove. FIGS. 6 and 7 are graphic representations of the potentiometric response of the resulting protamine-responsive membrane electrode over time as applied to direct potentiometric monitoring of urokinase activity. The protamine concentration in these experiments was 20 µg/ml. In FIG. 6, 278 units/ml of urokinase was added to the protamine solution, followed by the addition of 0.2 units/ml of plasminogen activator. In FIG. 7, 0.2 units/ml of plasminogen activator was added first to the protamine solution, followed by the addition of different concentrations of urokinase. The curves labelled "a," "b," and "c," on FIG. 7, represent 0, 3.3. and 278 units/ml of urokinase, respectively.

FIGS. 6 and 7 show a significant response to protamine per se ($\Delta E$=65 mV) upon the addition of 20 µg/ml of protamine to a test solution of Tris-HCl buffer (pH 7.4) containing 0.012M NaCl. However, the addition of urokinase or plasminogen alone to the protamine-containing test solution did not elicit any significant potential change, suggesting that neither urokinase nor plasminogen have proteolytic activity toward protamine. However, when plasminogen was subsequently added to the urokinase/protamine-containing solution (FIG. 7) or urokinase was subsequently added to the plasminogen/protamine-containing test solution (FIG. 6), a significant drop in potential was observed. This rapid change in potentiometric response is due primarily to the digestion of protamine by the newly generated plasmin. FIG. 7 demonstrates that the potential change is also related to the amount of urokinase added, or conversely, to the amount of plasmin generated.

Figure 8:
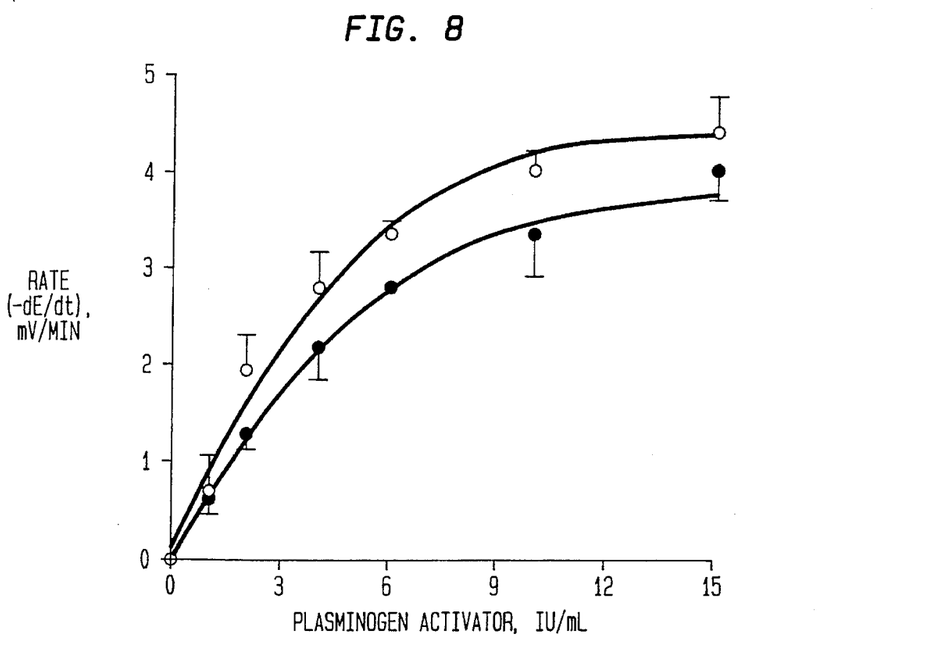
FIG. 8 is a graphic representation of the rate of potential decrease per unit of time ($-dE/dt$) as measured in mV/minute versus the activity of plasminogen activator added to the system, in IU/ml.

FIG. 8 is a graphic representation of the rate of potential decrease per unit of time (–dE/dt) as measured in mV/minute versus the activity of plasminogen activator added to the system, in IU/ml. The original system contained 20 µg/ml protamine in buffer (5 mM Tris-HCl) with 0.012 NaCl at pH 7.4. Each experiment was performed in triplicate so that the data are expressed as a mean±SD. Referring to FIG. 8, a linear relationship was observed for both streptokinase (data points designated "●") and urokinase (data points designated "o") at a concentration range between 0 to about 6 IU/ml. These results further confirm the feasibility of utilizing the protamine sensor of the present invention to monitor the activity of clinically-used thrombolytic drugs.

EXAMPLE 9

In as still further embodiments, the ion-selective polymer membrane electrode of the present invention exhibits response to small peptides with specially defined structures. An ion-selective polymer membrane electrode was fabricated, as described hereinabove, from a membrane having the following composition:

0.5 wt % potassium tetrakis(4-chlorophenyl) borate;

33 wt % 2-nitrophenyl octyl ether; and 66 wt % PVC.

Table VI shows the potentiometric response of the ion-selective polymer membrane electrode to 0.75 µg/ml of 7 different synthetic peptides labelled H1 to H7 in 5 mM Tris-HCl Buffer (pH 7.4) containing 12 mM NaCl. The peptides are listed in an amino acid sequence from the N-terminal to the C-terminal. The peptides labelled H5–H7 have been amidated at the C-Terminus.

TABLE VI

| Peptides | $\Delta E$ (mV) |
| --- | --- |
| H1: Val-Arg-Arg-Arg-Pro-Arg-Arg-Val-COOH | 7.9 |
| H2: Ser-Arg-Arg-Arg-Ser-Arg-Arg-Ser-COOH | 1.4 |
| H3: Val-Arg-Arg-Val-Val-Arg-Arg-Val-COOH | — |
| H4: Arg-Arg-Arg-Arg-Arg-Arg-Arg-Cys-COOH | 4.3 |
| H5: Val-Arg-Arg-Arg-Arg-Pro-Arg-Arg-Val-NH2 | 13.4 |
| H6: Val-Arg-Arg-Arg-Arg-Ala-Arg-Arg-Val-NH2 | 13.4 |
| H7: Phe-Arg-Arg-Arg-Phe-Val-Arg-Arg-Phe-NH2 | 26.9 |
| Protamine: | 12.7 |

As shown in Table VI, in order for the sensor to demonstrate significant response ($\Delta E$>10 mV), the peptide must possess at least an arginine trimer (i.e., Arg—Arg—Arg) and an arginine dimer sequence (i.e., Arg—Arg) connected by a hydrophobic amino acid residue, such as the proline residue in peptide H5 or the alanine residue in peptide H6. The stronger the hydrophobicity of the synthetic peptide, the stronger the potentiometric response evoked from the ion-sensing membrane. This is due, in no small measure, to the fact that a higher degree of the more hydrophobic peptide will be extracted into the hydrophobic polymer membrane matrix. Therefore, peptide H7, which has two hydrophobic residues (phenylalanine and valine) between the arginine trimer and dimer sequences, produced the greatest potential change, $\Delta E=26.9$ mV. On the other hand, neither arginine trimer nor pentamer alone elicited any significant responses from the ion-sensing membrane. A similar study was conducted with the preferred membrane of Example 8, and the same order of response, i.e., H7>H5, H6>H1, was observed.

Figure 9:
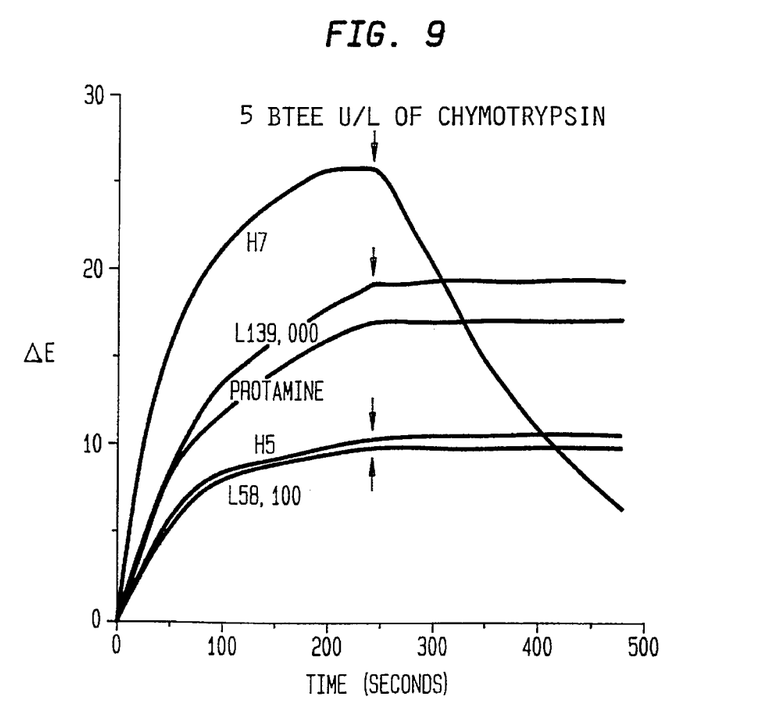
FIG. 9 is a graphic representation of the potentiometric response, $\Delta E$ in mV, of a protamine-responsive membrane electrode to digestion of specially designed synthetic peptides and protamine by chymotrypsin.

The response to synthetic peptides exhibited in Table VI indicates that the ion-selective polymer membrane sensor of the present invention could be used to measure the activity of other proteases, such as chymotrypsin, pepsin, and the like, using a specially designed synthetic substrate. FIG. 9 is a graphic representation of the potentiometric response, $\Delta E$ in mV, of the ion-selective membrane electrode of Example 9 to digestion of peptide H7, high molecular weight polylysine (M Wt 139,999 daltons), protamine, peptide H5, and low molecular weight polylysine (M Wt 58,100 daltons) with chymotrypsin. Since peptide H7 contains a phenylalanine residue, which is a cleavage site for the protease chymotrypsin, it is postulated that peptide H7 can be employed to measure chymotrypsin activity, using the ion-selective polymeric membrane sensor as a probe.

Referring to FIG. 9, the potentiometric response toward peptide H7 ($\Delta E=26$ mV), as measured in the presence of 0.75 μg/ml of the peptide only, was rapidly reduced by the addition of a substrate for chymotrypsin, N-benzoyl-L-tyrosine ethyl ester (BTEE, 5 unit/L chymotrypsin). The initial rate of digestion was proportional to the chymotrypsin activity. Although the other compounds tested exhibited significant potentiometric response to the ion-selective membrane, none were digested by chymotrypsin, primarily due to the lack of an adequate cleavage site. Peptide H7, however, could also be employed to monitor pepsin activity because it possesses the pepsin cleavage site (i.e., a valine residue).

EXAMPLE 10

In a still further method of use embodiment, the protamine-responsive sensor of the present invention was used to study the binding reactions of protamine with various types of heparins via classical potentiometric titrations. Since the potentiometric response of the sensor to free protamine levels is highly reproducible (±1 mV), the concentration of free protamine, after adding a given amount of protamine to a solution containing a known amount of heparin, can be assessed readily by the measured steady-state potential. Most conventional methods employed to study the binding of protamine to other macromolecules require the chemical modification of one of the macromolecules through labeling and/or an immobilization step (to separate bound from free). These chemical modifications can influence the binding reactions and, therefore, the values reported for binding constants and stoichiometrics may not reflect accurately the true strength or degree of interaction between the macromolecules in vivo.

Figure 10A:
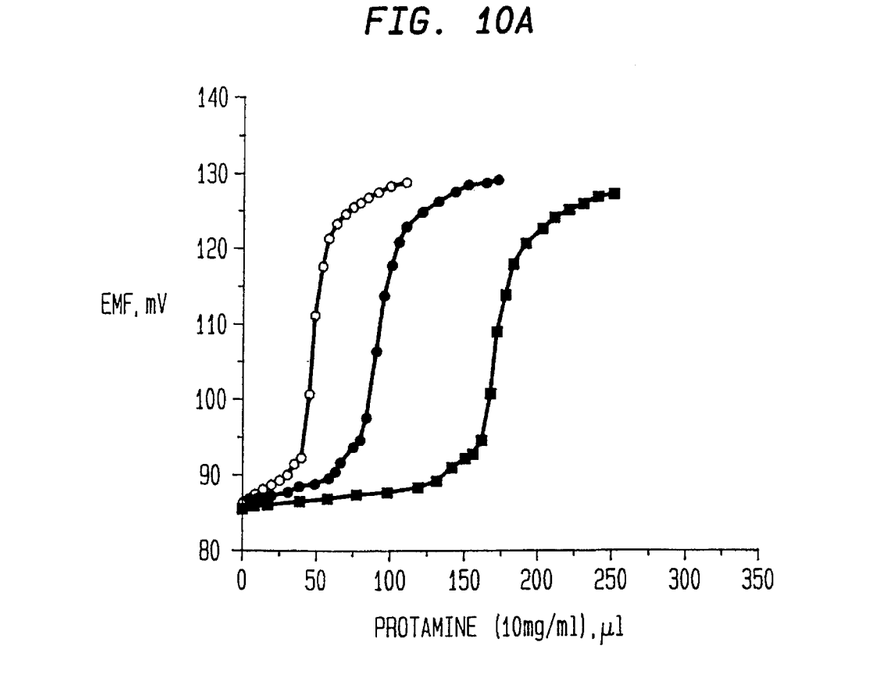
FIG. 10 is a graphic representation of potentiometric titration curves for two types of heparin, (A) porcine mucosal heparin and (B) bovine lung heparin, at three different concentrations ("o" for 50 USP units, "●" for 100 USP units, and "■" for 200 USP units) as neutralized by protamine measured by EMF (mV) plotted against μl of added protamine sulfate (10 mg/ml).
Figure 10B:
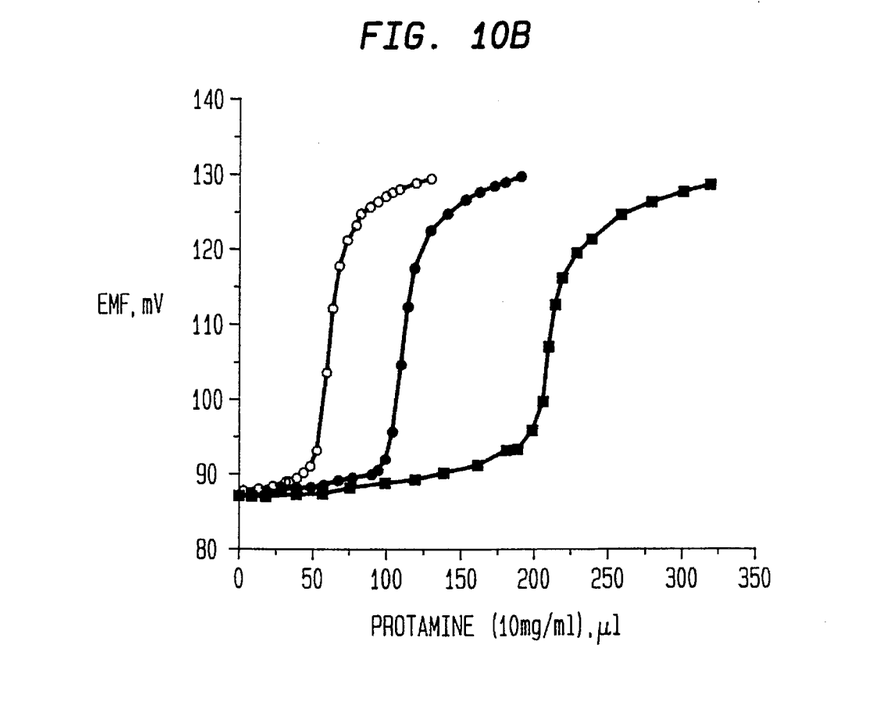

Potentiometric titrations of various heparin preparations were performed by adding small aliquots of a standard, concentrated protamine sulfate solution (10 mg/ml) to 50 ml of 0.12M NaCl solutions containing a fixed amount (50, 100, or 200 USP units) of either porcine or beef heparin. The solutions were stirred constantly during the titration procedures, which were carried out at room temperature (22° C.). FIG. 10 shows the potentiometric titration curves for titration with protamine sulfate of two types of heparin (A) porcine mucosal heparin and (B) bovine lung heparin at three different concentrations (data points designated as follows: "o" for 50 USP units, "●" for 100 USP units, and "■" for 200 USP units). The mass and molar stoichiometries for the binding reactions, as estimated from the endpoints of the titration curves, are summarized in Table VII.

TABLE VII

| Heparin (units/ml) | Neutralization endpoint (μl)$^{a,b}$ | | Protamine/heparin mass ratio | |
|---|---|---|---|---|
| | Porcine mucosa | Beef lung | Porcine mucosa | Beef lung |
| 50 | 42.8 ± 0.8 | 56.0 ± 1.3 | 1.44 ± 0.04 | 1.89 ± 0.05 |
| 100 | 84.5 ± 2.0 | 110.7 ± 2.2 | 1.43 ± 0.03 | 1.87 ± 0.04 |
| 200 | 166.4 ± 3.5 | 218.3 ± 3.7 | 1.41 ± 0.03 | 1.84 ± 0.04 |

The data on Table VII show that beef lung heparin requires about 20% more protamine than porcine mucosal heparin to neutralize a given amount. These results are in agreement with studies reported in the literature which state that 1 mg protamine is capable of neutralizing 100 USP units of gut-derived heparin but only 80 units of beef lung heparin.

In view of the foregoing, it is obvious that the protamine-responsive sensor of the present invention can be used for quality control of commercial heparin and/or protamine preparations. In addition, the protamine-responsive sensor can be used to study the binding of protamine to heparin, as well as a large number of other biologically important macromolecules, such as fibrinogen.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. An ion-responsive electrode membrane comprising, in admixture, a polymeric matrix material, lipophilic cation-exchange material, and, optionally, a plasticizer, the electrode membrane admixture formulation being selectively responsive to cationic hydrophobic macromolecules.

2. The ion-responsive electrode membrane of claim 1 wherein the cationic hydrophobic macromolecule is protamine.

3. The ion-responsive electrode membrane of claim 1 wherein the lipophilic cation-exchange material is a negatively charged lipophilic anion.

4. The ion-responsive electrode membrane of claim 3 wherein the negatively charged lipophilic anion is derived from a salt of an organoborate, organophosphate or organophosphonate.

5. The ion-responsive electrode membrane of claim 4 wherein the salt of organoborate is a salt of a tetraphenylborate selected from the group consisting of sodium tetraphenylborate, potassium tetrakis(4-chlorophenyl) borate, tetraphenylammonium tetraphenyl borate, sodium tetrakis[3, 5-bis(trifluoromethyl)phenyl]borate, and potassium tetrakis [3,5-bis(trifluoromethyl)phenyl]borate.

6. The ion-responsive electrode membrane of claim 5 wherein the salt of a tetraphenylborate is potassium tetrakis(4-chlorophenyl) borate.

7. The ion-responsive electrode membrane of claim 4 wherein the salt of an organophosphate or organophosphonate is selected from the group consisting of calcium bis-[4-(1,1,3,3-tetramethylbutyl)phenyl] phosphate, dioctylphenyl phosphonate, and tris (2-ethylhexyl) phosphate.

8. The ion-responsive electrode membrane of claim 7 wherein the salt of a organophosphate is calcium bis-[4-(1,1,3,3-tetramethylbutyl)phenyl] phosphate.

9. The ion-responsive electrode membrane of claim 1 wherein the polymeric matrix is a film-forming, hydrophobic polymer or copolymer.

10. The ion-responsive electrode membrane of claim 9 wherein the polymeric matrix material is selected from the group consisting of poly(vinyl chloride), polyurethane, cellulose triacetate, poly(vinyl alcohol)/poly(vinylchloride) copolymer, and silicone rubber.

11. The ion-responsive electrode membrane of claim 10 wherein the polymeric matrix material is poly(vinylchloride).

12. The ion-responsive electrode membrane of claim 1 wherein the plasticizer is one or more plasticizers selected from the group consisting of dioctyl phthalate, dioctyl sebacate, dioctyl adipate, dibutyl sebacate, dibutyl phthalate, 1-decanol, 5-phenyl-1-pentanol, tetraundecyl benzhydrol 3,3',4,4' tetracarboxylate, benzyl ether, dioctylphenyl phosphonate, tris(2-ethylhexyl) phosphate, and 2-nitrophenyl octyl ether.

13. The ion-responsive electrode membrane of claim 12 wherein the plasticizer is 2-nitrophenyl octyl ether.

14. The ion-responsive electrode membrane of claim 12 wherein the plasticizer is tris(2-ethylhexyl) phosphate.

15. The ion-responsive electrode membrane of claim 1 wherein analyte ions are equilibrated into the bulk of the polymeric matrix material but the outer surface layers of the polymeric matrix material are depleted of analyte ions.

16. An ion-responsive electrode membrane prepared by the process comprising:
    (a) forming an ion-responsive membrane comprising, in admixture, a polymeric matrix material and an ion-exchange material, and, optionally, a plasticizer, the ion-responsive membrane admixture formulation being responsive to a macromolecular analyte;
    (b) casting the ion-responsive membrane into a film;
    (c) conditioning the film with a concentrated solution of analtye ions for a period of at least 12–15 hours; and
    (d) exposing the film to a high-ionic strength solution for a short period of time to deplete the surface of the conditioned film of analyte ions.

17. A cation-responsive electrode membrane comprising, in admixture:
    0.1–5 wt % lipophilic cation-exchange material selective to cationic hydrophobic macromolecules;
    30 to 70 wt % plasticizer; and
    30 to 70 wt % polymer matrix material, the admixture formulation being optimized to selectively sense cationic hydrophobic macromolecules.

18. The cation-responsive electrode membrane of claim 17 wherein said ion-exchange material is present preferably in a weight percent of 1.0 to 2.0 wt %.

19. The cation-responsive electrode membrane of claim 17, wherein ratio of the plasticizer to the polymeric matrix material is in the range of 1 to 1.5.

20. A protamine-responsive polymeric membrane comprising:

1 wt % potassium tetrakis(4-chlorophenyl) borate;
49.5 wt % 2-nitrophenyl octyl ether; and
49.5 wt % poly(vinyl chloride).

21. A protamine-responsive polymeric membrane for sensing protamine in biological fluids comprising:
    1.0 wt % bis-[4-(1,1,3,3-tetramethylbutyl)phenyl] phosphate calcium salt;
    49.5 wt % tris (2-ethylhexyl) phosphate; and
    49.5 wt % PVC.

22. A membrane electrode having an ion-responsive membrane, the membrane electrode comprising:
    (a) a housing containing a reference solution;
    (b) an electrode arranged in the housing so that it is disposed in the reference solution; and
    (b) an ion-responsive membrane of a polymeric matrix material which is non-reactive with the liquid medium, an ion-exchange material, and, optionally, a plasticizer, the ion-responsive membrane being selective to protamine, the ion-responsive membrane being disposed on one end of the housing to seal the reference solution inside the housing and to contact a sample solution external to the housing.

23. A method of measuring the concentration of protamine in a liquid medium as a function of its potentiometric response, the method comprising:
    (a) bringing a membrane electrode having an ion-responsive membrane into contact with the liquid medium containing an unknown quantity of protamine, the ion-responsive membrane being characterized in that it comprises a polymeric matrix material which is non-reactive with the liquid medium, an ion-exchange material, and a plasticizer; and
    (b) measuring a potentiometric response which is indicative of the concentration of protamine in the liquid medium.

24. The method of claim 23 comprising the further steps of:
    (c) prior to bringing the membrane electrode into contact with the liquid medium containing an unknown quantity of protamine, pre-conditioning the membrane electrode in a concentrated solution of protamine for a period of at least 12–15 hours; and
    (d) following the step of pre-conditioning, exposing the film to a high-ionic strength solution for between about 1 and 10 minutes to deplete the surface of the conditioned film of protamine.

25. The method of measuring the concentration protamine of claim 23 wherein the ion-responsive membrane of the membrane electrode comprises 0.1 to 5 weight percent polymeric matrix material, 30 to 70 weight percent plasticizer, and 30 to 70 weight percent ion-exchange material.

26. The method of claim 23 wherein the liquid medium is a biological fluid, and the plasticizer is a salt selected from the group consisting of phosphates and phosphonates.

27. A method of monitoring protease activity comprising the steps of:
    (a) adding a proteolytic enzyme to a liquid medium containing a known amount of protamine or a synthetic peptide as a substrate for the proteolytic enzyme; and
    (b) measuring the change in concentration of protamine or synthetic peptide in the liquid medium as a function of its potentiometric response as the proteolytic enzyme degrades protamine into smaller fragments which do not produce a potentiometric response.

28. The method of claim 27 wherein the synthetic peptide comprises an amino acid sequence having at least an arginine trimer and an arginine dimer sequence connected by a hydrophobic amino acid residue.

29. A solid state membrane electrode for measuring the concentration of cationic macromolecules in a liquid medium as a function of potentiometric response comprising a conductive substrate and a membrane material arranged to be in adherence with said conductive substrate, said membrane material comprising a polymeric matrix material which is non-reactive with the liquid medium, an ion-exchange material, and, optionally, a plasticizer, said membrane being responsive to the cationic macromolecule.

30. A method of monitoring protease activity comprising the steps of:

(a) adding a proteolytic enzyme to a liquid medium containing a known amount of protamine or a synthetic peptide having an amino acid sequence with at least an arginine trimer and an arginine dimer sequence connected by a hydrophobic amino acid residue as a substrate for the proteolytic enzyme; and (b) measuring the change in concentration of protamine or synthetic peptide in the liquid medium as a function of its potentiometric response as the proteolytic enzyme degrades protamine into smaller fragments which do not produce a potentiometric response.

* * * * *